United States Patent [19]
Rapoport et al.

[11] 3,957,876
[45] May 18, 1976

[54] PROCESS FOR THE OXIDATION OF CYCLOHEXANE

[75] Inventors: Morris Rapoport; Jesse Oris White, both of Orange, Tex.

[73] Assignee: E. I. Du Pont de Nemours and Company, Wilmington, Del.

[22] Filed: May 30, 1973

[21] Appl. No.: 365,225

Related U.S. Application Data

[63] Continuation-in-part of Ser. No. 59,888, July 31, 1970, abandoned.

[52] U.S. Cl............................ 260/586 P; 260/631 R; 260/610 B
[51] Int. Cl.².................. C07C 179/02; C07C 49/30
[58] Field of Search.......... 260/610 B, 586 B, 631 R

[56] References Cited
UNITED STATES PATENTS

| | | |
|---|---|---|
| 2,618,662 | 11/1952 | Hutchinson..................... 260/610 A |
| 2,825,742 | 3/1958 | Schueler et al..................... 260/586 |
| 2,851,496 | 9/1958 | Cates et al.......................... 260/586 |
| 3,510,526 | 5/1970 | Bonnart et al. ................. 260/610 B |

Primary Examiner—Bernard Helfin
Assistant Examiner—W. B. Lone

[57] ABSTRACT

Preparation of cyclohexyl hydroperoxide substantially free of other peroxides by oxidation of cyclohexane containing a cyclohexane soluble cobalt salt in a zoned oxidation process in which an oxygen containing gas is fed to each zone in the oxidation section in an amount in excess of that which will react under the conditions of that zone.

3 Claims, 1 Drawing Figure

U.S. Patent    May 18, 1976    3,957,876
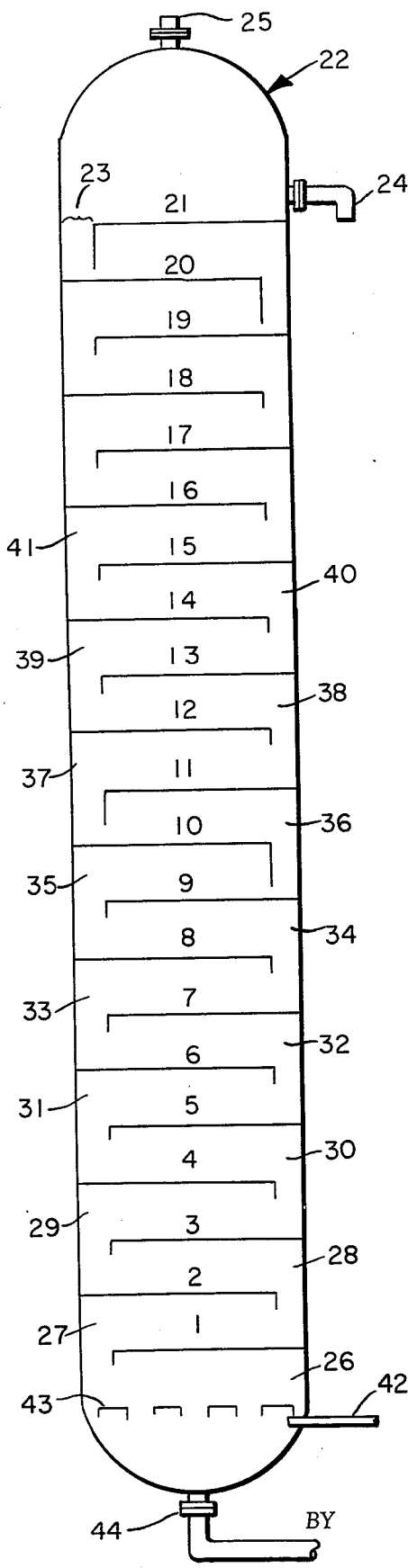
INVENTORS
MORRIS RAPOPORT
JESSE ORIS WHITE
BY  *Earl L. Handley*
ATTORNEY 3,957,876

PROCESS FOR THE OXIDATION OF CYCLOHEXANE

CROSS-REFERENCE TO RELATED APPLICATIONS

This is a continuation-in-part of U.S. patent application Ser. No. 59,888, filed by M. Rapoport and J. O. White on July 31, 1970 and now abandoned, disclosures of which are incorporated herein by reference.

BACKGROUND OF THE INVENTION

It is known in the art (British No. 777,087) that cyclohexyl hydroperoxide (CHHP) is formed in the air oxidation of cyclohexane (cyane) along with cyclohexanone and cyclohexanol. It is also well recognized that cyclohexanol and cyclohexanone can be converted by oxidation to adipic acid and that CHHP can be converted to cyclohexanone (K) or cyclohexanol (A) either in the course of the cyane oxidation or in a separate decomposition or conversion step.

The development of processes for providing an optimum yield of adipic acid from these several intermediates has been the subject of extensive effort. Because CHHP may be used as an oxidizing agent for various purposes such as the oxidation of olefin materials, as well as an intermediate to the adipic acid precursors, K and A, cyane oxidation processes have been sought which would give a high proportion of CHHP in the reaction product.

In U.S. Pat. No. 2,851,496 there is described a process for oxidizing cyane with or without a catalyst to give the corresponding hydroperoxide (CHHP) along with the adipic acid precursors K and A, and thereafter converting or decomposing the CHHP into K and A by heating in the presence of a decomposition catalyst.

In U.S. Pat. No. 3,530,185 there is described a multi-step process wherein cyane with or without catalyst is oxidized to give primarily K and A with lesser amounts of CHHP. In general, as stated in U.S. Pat. No. 3,530,185 and noted also in Japanese publication *Oxidation*, published by Kagaku Kogyo Sha, Aug. 10, 1963, pages 144–146, if catalyst is present the CHHP tends to be decomposed and the main products are K and A.

It is further known that in the air oxidation of cyane in the absence of a catalyst a high proportion of the oxidized products is in the form of CHHP. In U.S. Pat. No. 3,510,526 a process is described which gives high yields of hydroperoxide by the air oxidation of a cycloalkyl compound such as cyane in the absence of a catalyst, in apparatus previously rendered passive by treatment with sodium pyrophosphate to minimize any catalytic effects of the equipment and with the added step on treating recycled cycloalkane with base to remove acidic by-products. Obtaining an increased yield of hydroperoxide by carrying out the oxidation in presence of an aqueous solution of an alkali metal or calcium pyrophosphate has also been described (U.S. Pat. No. 2,798,096).

As noted above, air oxidation of cyane gives rise to the adipic acid precursors K and A as well as CHHP, which in turn can be converted to K and A. A complication attending the use of the various processes described is that appreciable amounts of peroxides other than CHHP may also be formed in the air oxidation of cyane and these also can undergo decomposition or conversion but to products other than K and A. This is indicated to be the case in U.S. Pat. No. 2,851,496, in U.S. Pat. No. 3,530,185 and in U.S. Pat. No. 3,719,706, the latter of which describes a process for isolating and utilizing a peroxide other than CHHP, namely 6-hydroperoxyhexanoic acid.

Accordingly, a process has been sought for air oxidation of cyane which would provide a product stream containing a high proportion of CHHP along with K and A and which would be substantially free of peroxides other than CHHP.

SUMMARY OF THE INVENTION

A process has now been found for the oxidation of cyclohexane to a product fluid consisting essentially of unreacted cyclohexane, cyclohexanone, cyclohexanol and a high proportion of cyclohexyl hydroperoxide, the product fluid being substantially free of peroxides other than cyclohexyl hydroperoxide. The process is carried out by oxidizing cyclohexane (cyane) in a series of zones wherein cyane is fed downwardly through the zones and an oxidizing gas (gas containing molecular oxygen) is passed upwardly through the zones, the conditions being such that the amount of oxygen present in each reaction zone is in excess of that which will react under the particular conditions of that zone. The upward passing oxidizing gas after proceeding through the oxidizing zones is conducted through a series of oxygen cleanup zones wherein the oxygen content is reduced. On condensing the resulting off-gas from the reaction to reclaim unreacted cyclohexane the oxygen level is such that an explosive mixture is never formed. A suitable apparatus for carrying out the zoned oxidation is shown in the FIGURE, which is a sectional view of a tower oxidizer.

To carry out the process of the present invention, the cyclohexane to be oxidized must contain a cobalt catalyst in the amount of about 0.1 to 5 parts per million parts of "product fluid". The term product fluid is defined as the fluid recovered exit the lowest oxidizing zone, the fluid containing cyclohexane, cyclohexanol, cyclohexanone, cyclohexyl hydroperoxide and other oxidation products in minor amounts. More catalyst than the 5 parts per million results in significantly lower amounts of cyclohexyl hydroperoxide, because the peroxide at higher catalyst levels decomposes and reacts with the cyclohexane and thus cannot be recovered. At catalyst levels lower than 0.1 part per million the reaction becomes inefficient in that by-products including peroxides other than CHHP are produced and productivity as to desired products is lowered. Suitable cobalt catalysts include cobalt compounds, particularly cobalt salts of carboxylic acids, which are soluble in cyclohexane, such as cobalt naphthenate, cobalt octoate, cobalt laurate, cobalt palmitate, cobalt stearate, cobalt linoleate and cobalt acetylacetonate. The cobalt catalyst can be a cobalt salt as indicated above or as the reaction proceeds and product fluid as well as catalyst compounds are recycled to the process the catalyst may be in the form of cobalt salt of an organic acid produced in the course of the cyclohexane oxidation. An essential requirement is that the cobalt compound be soluble in cyclohexane so that it can be intimately associated with the cyclohexane in the course of its oxidation. Pyrophosphate salts may also be present along with the above-mentioned catalysts.

As is illustrated in the accompanying FIGURE, details of which are discussed in the Description of Preferred Embodiments, cyclohexane containing the cobalt catalyst is first passed through a series of zones of oxygen cleanup where the cyclohexane is contacted and reacted with the gas that has been previously reacted with cyclohexane in the oxidation zone. The oxygen cleanup zone is operated at a temperature in the range of 130° to 180°C. and at a pressure of 60 to 350 psig. as measured at the top of the cleanup zone. In the oxygen cleanup zone most of the oxygen remaining in the gas that had previously contacted and reacted with cyclohexane in the oxidizing zones reacts further with cyclohexane so that the gas leaving the top of the reactor contains only a very low concentration of oxygen. The oxygen concentration in this off-gas measured after the cyclohexane condensation should be less than 4 mole % so that the gas will not form an explosive mixture.

After passing through the oxygen cleanup zones, the cyclohexane passes into a series of oxidizing zones. These zones are maintained at a temperature in the range of 140° to 170°C., and since they are in the same reactor as the oxygen cleanup zones the pressure is in the same range as the oxygen cleanup zones: 60–350 psig as measured at the top of the cleanup zones. The temperature may vary from one oxidizing zone to another. In each oxidizing zone the concentration of the oxygen in the gas is kept at a level in excess of the amount of oxygen that will react with the cyclohexane feed in that zone; this is accomplished by adding the oxidation gas, usually air, at each zone. In addition, no more than 95% of the total oxygen fed to the oxidizing zones should be consumed in the oxidizing zones.

After passing through the oxidizing zones, the product fluid is recovered. The product fluid will contain in addition to cyclohexane, cyclohexanol, cyclohexanone, cyclohexyl hydroperoxide, other oxidation products in minor amounts, but substantially no peroxides other than cyclohexyl hydroperoxide. The percentage by weight of cyclohexyl hydroperoxide to the total of cyclohexanol, cycohexanone and cyclohexyl hydroperoxide as measured at the exit of the lowest oxidizing zone will be greater than 15%.

Moreover, this process is useful where the extent of oxidation is such that the ratio, total air rate/product rate $$\frac{(Mscfh)}{(gpm)}$$

is in the range of 0.1 to 0.7. Mscfh is defined as thousands standard cubic feet per hour, and gpm is defined as gallons per minute.

The product fluid may then be employed as an oxidizing agent for olefins or it may be converted to K and A in a separate step as described in British Patent No. 777,087, or by carrying out the conversion in a lower part of the tower reactor.

The advantages of the process of this invention over those of the prior art are that (1) the oxidized product contains a high proportion of cyclohexyl hydroperoxide (2) the oxidized product is substantially free of peroxide other than cyclohexyl hydroperoxide, (3) the process does not require passivation of the oxidation equipment and (4) process streams do not require treatment, for example, with alkaline solution before recycle to the process. Furthermore, even though the process is carried out with an excess of oxygen in the oxidizing zones, the incorporated oxygen cleanup feature provides for safe operation of this improved process.

DESCRIPTION OF PREFERRED EMBODIMENTS

The examples which follow are carried out in a reactor such as that illustrated in the FIGURE. The reactor 22, made of any suitable material such as 316 stainless steel, contains 21 equally spaced trays designated 1–21. The reactor height to diameter ratio is 8, and the downcomer opening 23 cross-sectional area for each tray to tower cross-sectional area is 0.12. The tower has inlet port 24 through which cyclohexane which contains a soluble salt of cobalt is introduced into the reactor, and off-gas port 25 through which the gaseous vapor containing relatively small amounts of oxygen is removed from the reactor. The catalyst may also be introduced at one or more other points in the oxygen cleanup zones. Each tray 1–21 contains a number of apertures (not shown) through which the oxidizing gas passes on way up the tower. Oxidizing gas may be fed to any or all of the first 18 trays. Since each tray must accommodate not only the gas fed to it alone but also gases from the trays below, the number and/or size of the apertures is progressively greater from the bottom to the top of the reactor. In examples where the lower 15 trays were used oxidizing gas was added at points designated 26–40, inclusive. The average free tray area (i.e., the area of the apertures in the trays) for all of the trays to tower cross-sectional area may vary widely but for the examples set forth below it is 1.2% calculated according to the following equation:

$$\frac{\text{Average free tray area} \times 100}{\text{Tower cross-sectional area}} = 1.2\%$$

Recycled off-gas after removal of most of the contained cyane, K and A is introduced through inlet 42 through spargers 43. Outlet port 44 is used to remove the product continuously from the reactor. Sampling devices (not shown) to sample the gas or liquid may be inserted through reactor if desired, at selected locations.

In operation the cyclohexane to be oxidized is introduced through inlet 24. It passes over tray 21 and the gas under tray 21 bubbles through the holes in tray 21 and through the cyclohexane. This flow across each tray while being subjected to the gas treatment is repeated as the cyclohexane moves down the tower.

If desired, the oxidizing gas feed may be shut off at trays lower than tray 16, and thus increases the length of the oxygen cleanup zone (See Example 5).

Recycled gas is introduced at 42 through sparger 43 to increase the volume of gas moving up the tower and thus providing mild oxidizing conditions throughout the tower, while at the same time stripping cyclohexane from the product fluid.

The conditions used and results obtained in runs using cobalt naphthenate catalyst (Examples 1–5, 7, 8) and cobalt octoate (Example 6) are summarized in Table I. The peroxide composition of a typical run (Example 8) was determined as described below.

It has been shown in the literature that the reaction of triphenylphosphine with hydroperoxides to form the corresponding alcohols is a general reaction as follows:

$$R'OOH + R_3P \rightarrow R'OH + R_3PO$$

Accordingly, 10 kilograms of the product fluid from Example 8 was reacted with triphenylphosphine ($\phi_3P$) according to the procedures described by L. Harner and W. Hurgeleit, *Ann.* 591, 138 (1955); L. Dulog and K. H. Burg, *Z. Anal. Chem.* 203, 184 (1964); D. B. Denny, W. F. Goodyear and B. Goldstein, *JACS*, 1393

(1960). Before and after treatment with triphenylphosphine the product fluid was analyzed for peroxides by a standard iodometric method (Mair, R. O and Graupner, A. J., *Anal. Chem.* 36, 194 (1964) and for cyclohexanol by a gas chromatographic method. The results, summarized below, show that the number of moles of cyclohexanol formed (0.7728) and the number of equivalents of peroxide (0.7774) consumed are essentially the same. Thus, the peroxides in the product fluid are essentially all cyclohexylhydroperoxide and do not contain significant quantities of other peroxides.

| | Analysis of Product Fluid | | |
|---|---|---|---|
| | Before Reaction with $\phi_3P$ | After Reaction of $\phi_3P$ | Change |
| Equivalents of Peroxide | 0.7774 | 0 | 0.7774 |
| Moles of Cyclohexanol | 0.6789 | 1.4517 | 0.7728 |

TABLE I

CYCLOHEXANE OXIDATION

| | Ex.1 | Ex.2 | Ex.3 | Ex.4 | Ex.5 | Ex.6 | Ex.7 | Ex.8 |
|---|---|---|---|---|---|---|---|---|
| No. of Oxygen Cleanup Trays | 6 | 6 | 6 | 6 | 13 | 6 | 3 | 3 |
| No. of Air Feed Trays | 15 | 10 | 15 | 15 | 8 | 5 | 18 | 18 |
| Actual Oxygen Cleanup Trays | 16–21 | 16–21 | 16–21 | 16–21 | 9–21 | 16–21 | 19–21 | 19–21 |
| Actual Air Feed Trays | 1–15 | 6–15 | 1–15 | 1–15 | 1–8 | 11–15 | 1–18 | 1–18 |
| Ratio of $\frac{\text{Recycle Gas Rate}}{\text{Product Rate}}$, $\left(\frac{\text{scfh}}{\text{lbs per hr}}\right)$ | 0.63 | 0.54[2] | 0.66 | 0.39 | 0.67 | 0.31 | 0.31 | 0 |
| Ratio of $\frac{\text{Total Air Rate}}{\text{Product Rate}}$, $\left(\frac{\text{scfh}}{\text{lbs per hr}}\right)$[1] | 1.08 | 1.11 | 1.34 | 0.85 | 0.87 | 0.60 | 0.79 | 0.44 |
| Product Rate, parts per hour[9] | 440 | 440 | 432 | 380 | 429 | 350 | 1071 | 2029 |
| Feed Rate, parts per hour | 530 | 520 | 500 | 405 | 540 | 412 | 1366 | 2263 |
| Cyclohexane recovered from off-gas, parts per hour | 90 | 80 | 68 | 25 | 111 | 62 | 295 | 234 |
| Ratio, $\frac{\text{Total Air Rate}}{\text{Product Rate}}$, $\left(\frac{\text{M scfh}}{\text{gpm}}\right)$ | 0.36 | 0.37 | 0.45 | 0.28 | 0.29 | 0.20 | 0.26 | 0.14 |
| Catalyst Concentration, ppm Co (introduced at Tray 19)[3] | 0.7 | 0.8 | 0.8 | 2.1 | 0.8 | 0.5[10] | 0.5[12] | 0.5[12] |
| Oxygen Conc. (mol % $O_2$, Dry Basis)[8] | | | | | | | | |
| Off-gas | 1.0 | 0.9 | 1.02 | 0.8 | 1.4 | 0.35 | 3.78 | 2.32 |
| Tray 17 | 2.2 | 2.4 | 1.76 | 1.18 | 1.74 | 1.1[11] | 5.1[11] | 4.6[11] |
| Tray 14 | 1.8 | 2.8 | 2.02 | 1.30 | 3.24 | 2.5[11] | 5.2[11] | 5.5[11] |
| Tray 11 | 1.0 | 0.7 | 0.96 | 0.60 | 4.20 | 0.4[11] | 5.2[11] | 6.4[11] |
| Tray 8 | 0.8 | 0.4 | 0.92 | 0.36 | 6.6[4] | — | 5.5[11] | 7.7[11] |
| Tray 5 | 0.9 | 0[5] | 0.86 | 0.58 | — | — | 5.8[11] | 10.3[11] |
| Tray 2 | 0.5 | 0[5] | 0.48 | 0.12 | — | — | 5.4[11] | 12.2[11] |
| Mol % Oxygen Consumed in Oxidation Zone | 86 | 85 | 88 | 93 | 54 | 74[11] | 70[11] | 83[11] |
| Mol % Oxygen Consumed in Cleanup Zone | 8 | 10 | 6 | 2 | 36 | 24 | 8 | 8 |
| Mol % Oxygen Unreacted | 6 | 5 | 6 | 5 | 10 | 2 | 22 | 9 |
| Wt. % Total of cyclohexanone, cyclohexanol & cyclohexyl hydroperoxide in bottom oxidation tray | 4.91 | 4.59[6] | 5.67 | 4.26 | 3.62 | 2.88 | 2.85[13] | 1.91 |
| Wt. % cyclohexyl hydroperoxide in bottom oxidation tray | 1.37 | 0.93[6] | 1.26 | 1.00 | 0.84 | 1.08 | 1.29[13] | 0.90 |
| Wt % $\left(\frac{\text{cyclohexyl hydroperoxide} \times 100}{\text{cyclohexyl hydroperoxide + cyclohexanone + cyclohexanol in bottom oxidation tray}}\right)$ | 27.9 | 20.3[6] | 22.2 | 23.5 | 23.5 | 37.5 | 45.1[13] | 47.2 |
| Wt % cyclohexanone + cyclohexanol + cyclohexyl hydroperoxide in product | 5.22 | 4.85 | 6.19 | 4.46 | 3.92 | 3.11 | 3.06 | 1.91 |
| Cyclohexyl hydroperoxide production rate exit lowest oxidizing zone, parts per hr[7] | 6.41 | 4.33[6] | 5.94 | 3.98 | 3.90 | 4.08 | 14.78 | 18.32 |
| Back Pressure, psig | 120 | 125 | 130 | 112 | 115 | 135 | 154 | 152 |
| Tower Temp. Profile, °C. | | | | | | | | |
| Tray 21 | 138 | 135 | 131 | 113 | 129 | 138 | 162 | 170 |
| Tray 20 | 148 | 146 | 143 | 120 | 140 | 141 | 162[14] | 169[14] |
| Tray 15 | 154 | 157 | 159 | 146 | 154 | 155 | 160[14] | 168[14] |
| Tray 11 | 157 | 160 | 162 | 155 | 152 | 159 | 161[14] | 168[14] |
| Tray 10 | 156 | 160 | 162 | 154 | 151 | — | 161 | 167 |
| Tray 5 | 156 | 155 | 163 | 157 | 144 | — | 160[14] | 167[14] |
| Tray 1 | 150 | 151 | 155 | 153 | 142 | — | 155 | 166 |
| Product | 142 | 148 | 147 | 146 | 134 | — | 153[14] | 166[14] |

[1] The total air used is distributed equally among all the air feed trays.
[2] Recycle gas distributed 37% to base and 63% to Trays 1–5.
[3] Calculated on product rate basis, cobalt naphthenate used in Examples 1–5, 7, 8; cobalt octoate used in Example 6
[4] Estimated exit Tray 8
[5] Tray 6 is the bottom oxidation tray
[6] Tray 5 compositions, one tray lower than the bottom oxidation tray

[7] Cyclohexyl hydroperoxide flow rate = Product flow rate $\times \left(\frac{\text{Wt. \% product cyclohexanone + cyclohexanol hydroperoxide}}{100}\right)$ $\times \left(\frac{\text{Wt. \% cyclohexyl hydroperoxide/ cyclohexanone + cyclohexanol + cyclohexyl hydroperoxide}}{100}\right)$ The mass flow of cyclohexanone + cyclohexanol + cyclohexyl hydroperoxide exit the oxidation zone is essentially equal to the mass flow of cyclohexanone + cyclohexanol + cyclohexyl hydroperoxide in the product.
Other salts of cobalt that are soluble in cyclohexane may be used as a catalyst for the reaction.

TABLE I-continued

CYCLOHEXANE OXIDATION
Ex.1　Ex.2　Ex.3　Ex.4　Ex.5　Ex.6　Ex.7　Ex.8

(8)Does not include the oxygen in the air feed to the designated tray.
(9)Defined as the rate of product exit the reactor at outlet port 44.
(10)Catalyst introduced at Tray 20.
(11)Calculated from cyclohexane oxidized.
(12)Catalyst concentration in feed.
(13)Calculated from tails concentration and cyclohexane vaporized.
(14)Interpolated from trays immediately above and below.

We claim:

1. A process for the oxidation of cyclohexane to produce a product fluid consisting essentially of unreacted cyclohexane, cyclohexanone, cyclohexanol, and cyclohexyl hydroperoxide, the percentage of cyclohexyl hydroperoxide to the total of cyclohexanone, cyclohexanol and cyclohexyl hydroperoxide being greater than 15% by weight, the product fluid being substantially free of peroxides other than cyclohexyl hydroperoxide, which consists essentially of passing a fluid containing cyclohexane and a cyclohexane soluble cobalt salt selected from the class consisting of cobalt naphthenate, cobalt octoate, cobalt laurate, cobalt palmitate, cobalt stearate, cobalt linoleate, cobalt acetylacetonate and mixtures thereof in the amounts of 0.1 to 5 parts per million parts of product fluid downwardly through a series of oxygen cleanup zones and oxidizing zones at a pressure measured at the top of the oxygen cleanup zone of 60–350 psig. while countercurrently passing an oxidizing gas containing molecular oxygen upwardly through the zones, the fluid initially passing through a series of oxygen cleanup zones wherein the temperature is maintained in the range of 130° to 180°C. and where the oxygen concentration in the upward passing gas leaving the oxygen cleanup zone is reduced to less than 4 mole percent, the fluid then passing through a series of oxidizing zones operated at a temperature in the range of 140°–170°C. in which the level of oxygen is maintained at a level in excess of the amount of oxygen that will react with the fluid mixture under the particular conditions of that zone by addition of oxidizing gas to that zone, the overall amount of oxygen consumed in the oxidizing zones being not more than 95 mole % of the amount fed;

and recovering product fluid containing cyclohexane, cyclohexanol, cyclohexanone and cyclohexyl hydroperoxide at the exit of the lowest oxidizing zone.

2. The process of claim 1 in which the gas obtained after passing through the oxygen cleanup zone is condensed to remove the cyclohexane and a portion of this gas is then introduced at the bottom of the oxidation zone.

3. The process of claim 1 where the ratio, total air rate/product rate (M scfh/gpm) is in the range 0.1 to 0.7.

* * * * *